US010583616B2

(12) United States Patent
Georgeson et al.

(10) Patent No.: US 10,583,616 B2
(45) Date of Patent: Mar. 10, 2020

(54) FORMING TOOLS AND FLEXIBLE ULTRASONIC TRANSDUCER ARRAYS (71) Applicant: The Boeing Company, Chicago, IL (US)

(72) Inventors: Gary E. Georgeson, Tacoma, WA (US); Jeffrey R. Kollgaard, Seattle, WA (US); Tyler M. Holmes, Seattle, WA (US)

(73) Assignee: The Boeing Company, Chicago, IL (US)

( * ) Notice: Subject to any disclaimer, the term of this patent is extended or adjusted under 35 U.S.C. 154(b) by 909 days.

(21) Appl. No.: 14/311,016

(22) Filed: Jun. 20, 2014

(65) Prior Publication Data

US 2015/0367586 A1 Dec. 24, 2015

(51) Int. Cl.
B29C 70/68 (2006.01)
B29C 70/34 (2006.01)
G01N 29/04 (2006.01)
B29C 70/86 (2006.01)
G01N 29/22 (2006.01)
B06B 1/06 (2006.01)
B29C 70/88 (2006.01)
G01N 29/24 (2006.01)
B29L 9/00 (2006.01)
B29C 73/10 (2006.01)

(52) U.S. Cl.
CPC .......... B29C 70/342 (2013.01); B06B 1/0629 (2013.01); B06B 1/0688 (2013.01); B29C 70/865 (2013.01); B29C 70/882 (2013.01); G01N 29/043 (2013.01); G01N 29/227 (2013.01); G01N 29/228 (2013.01); G01N 29/2437 (2013.01); B29C 73/10 (2013.01); B29L 2009/00 (2013.01); G01N 2291/0231 (2013.01); G01N 2291/044 (2013.01); G01N 2291/048 (2013.01); G01N 2291/106 (2013.01)

(58) Field of Classification Search
CPC combination set(s) only.
See application file for complete search history.

(56) References Cited

U.S. PATENT DOCUMENTS 3,741,117 A * 6/1973 Bienert ............... B41M 1/42
101/489
4,455,268 A * 6/1984 Hinrichs ............ B29C 35/0288
264/236
4,559,810 A * 12/1985 Hinrichs ................ B01J 3/002
73/54.41
4,856,335 A * 8/1989 Tornberg ............... G01N 29/07
73/597
5,423,220 A * 6/1995 Finsterwald .......... B06B 1/0622
310/322

(Continued)

OTHER PUBLICATIONS

Langlois—Use of Flexible Ultrasonic Arrays in Inspection—Mar. 1999—vol. 4 No. 3; NDT.net.*

(Continued)

Primary Examiner — Isam A Alsomiri
Assistant Examiner — Amie M Ndure
(74) Attorney, Agent, or Firm — Miller, Matthias & Hull LLP (57) ABSTRACT An apparatus comprises a forming tool having a forming surface, and an ultrasonic transducer array on the forming surface.

13 Claims, 7 Drawing Sheets

(56) References Cited

U.S. PATENT DOCUMENTS

| | | | | |
|---|---|---|---|---|
| 5,637,800 | A | * | 6/1997 | Finsterwald ........ B06B 1/0622 73/642 |
| 5,680,863 | A | * | 10/1997 | Hossack ................ A61B 8/12 600/437 |
| 5,711,058 | A | * | 1/1998 | Frey .................... B06B 1/0622 29/25.35 |
| 6,254,812 | B1 | * | 7/2001 | Goodridge ........... B29C 33/303 249/178 |
| 6,321,428 | B1 | * | 11/2001 | Toda .................... B06B 1/0688 29/25.35 |
| 6,585,839 | B2 | * | 7/2003 | Woods ............... B29C 66/1122 156/308.2 |
| 7,240,556 | B2 | * | 7/2007 | Georgeson ........... G01N 29/041 73/620 |
| 7,617,730 | B2 | * | 11/2009 | Georgeson ......... G01N 29/0645 73/602 |
| 7,712,369 | B2 | * | 5/2010 | Georgeson ............ G01N 29/04 73/602 |
| 7,785,098 | B1 | * | 8/2010 | Appleby .............. B29C 33/302 264/319 |
| 8,333,115 | B1 | * | 12/2012 | Garvey ............... G01N 29/043 73/632 |
| 8,453,928 | B2 | * | 6/2013 | Melandso ................ G06K 7/02 235/439 |
| 8,662,395 | B2 | * | 3/2014 | Melandso ................ G06K 7/02 235/439 |
| 9,315,663 | B2 | * | 4/2016 | Appleby ................ C08L 63/00 |
| 9,816,854 | B2 | * | 11/2017 | Kudlaty ............... B06B 1/0292 |
| 2001/0030281 | A1 | * | 10/2001 | Schulz ................. G01M 3/165 250/227.21 |
| 2002/0087083 | A1 | * | 7/2002 | Nix .......................... A61B 8/12 600/459 |
| 2002/0154029 | A1 | * | 10/2002 | Watters ................... G01D 5/48 340/870.07 |
| 2003/0009300 | A1 | * | 1/2003 | Giurgiutiu ............. G01N 29/11 702/35 |
| 2003/0029010 | A1 | * | 2/2003 | Aime .................. G10K 11/002 29/25.35 |
| 2003/0066356 | A1 | * | 4/2003 | Kanellopoulos ........ G01L 1/246 73/800 |
| 2003/0093187 | A1 | * | 5/2003 | Walker ................... B64C 13/20 701/1 |
| 2006/0027308 | A1 | * | 2/2006 | MacKenzie ............. B29C 73/10 156/94 |
| 2006/0201252 | A1 | * | 9/2006 | Georgeson ........... G01N 29/041 73/641 |
| 2008/0272968 | A1 | * | 11/2008 | Muller ................... H01Q 1/225 343/703 |
| 2008/0309200 | A1 | * | 12/2008 | Melandso ............... B06B 1/064 310/334 |
| 2009/0133501 | A1 | * | 5/2009 | Georgeson ............. G01N 29/04 73/632 |
| 2009/0259411 | A1 | * | 10/2009 | Loomis .................... G01B 7/16 702/35 |
| 2011/0086199 | A1 | * | 4/2011 | Duqueine ............. B29C 70/202 428/112 |
| 2011/0132523 | A1 | * | 6/2011 | Evens ..................... B29C 73/10 156/94 |
| 2011/0189440 | A1 | * | 8/2011 | Appleby ..................... B22C 9/04 428/156 |
| 2012/0253698 | A1 | * | 10/2012 | Cokonaj ............... B06B 1/0622 702/39 |
| 2013/0075526 | A1 | * | 3/2013 | Griess ....................... B32B 5/26 244/123.1 |
| 2013/0192356 | A1 | * | 8/2013 | De Graff ................... F41H 1/04 73/152.01 |
| 2014/0133987 | A1 | * | 5/2014 | Guinaldo Fernandez ................... B64C 3/28 416/131 |
| 2014/0316551 | A1 | * | 10/2014 | Ellis ........................ G01N 27/90 700/127 |
| 2015/0344138 | A1 | * | 12/2015 | Wen ....................... H05B 3/286 219/541 |

OTHER PUBLICATIONS

Shih et al, "Applications of Flexible Ultrasonic Transducer Array for Defect Detection at 150 ° C.," ISSN 1424-8220, www.mdpi.com/journal/sensors.

Bowen et al., "Flexible piezoelectric transducer for ultrasonic inspection of non-planar components," Ultrasonics 48 (2008) 367-375.

* cited by examiner

FORMING TOOLS AND FLEXIBLE ULTRASONIC TRANSDUCER ARRAYS

BACKGROUND

Ultrasonic testing is commonly used in the aircraft industry to validate the health (e.g., integrity and fitness) of aircraft structures. The testing may be performed by scanning an ultrasonic transducer array over a surface of a structure. For large structures, the transducer array may be scanned with a robotic multi-axis scanning system.

SUMMARY

According to an embodiment herein, an apparatus comprises a forming tool having a forming surface, and an ultrasonic transducer array on the forming surface.

According to another embodiment herein, a method comprises placing an uncured ply stack and a flexible ultrasonic transducer array on a forming surface of a forming tool.

According to another embodiment herein, an article comprises a cured fiber reinforced plastic part and a flexible ultrasonic transducer array embedded in the cured part.

These features and functions may be achieved independently in various embodiments or may be combined in other embodiments. Further details of the embodiments can be seen with reference to the following description and drawings.

DETAILED DESCRIPTION

Figure 1:
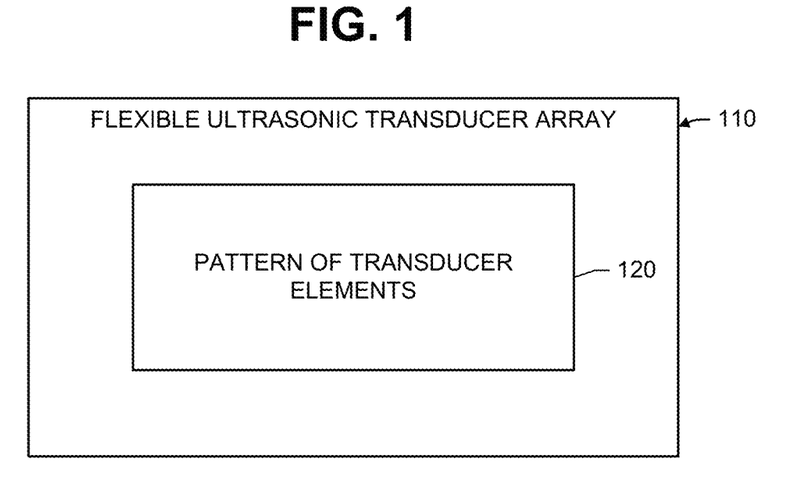
FIG. 1 is an illustration of a flexible ultrasonic transducer array.

Reference is made to FIG. 1, which illustrates a flexible ultrasonic transducer array 110. The transducer array 110 includes a plurality of transducer elements 120 arranged in a pattern. The transducer elements 120 are not limited to any particular pattern. In some instances, the pattern may be a grid (e.g., square, rectangular, triangular) of the transducer elements 120.

The transducer array 120 is not limited to any particular construction. As a first example, a transducer array 120 includes a pattern of individual elements 120.

As a second example, the transducer array 110 includes a thin metal foil, a film of piezoelectric material on the foil, and top electrodes on film. The thin metal foil serves as a substrate and base electrode and may be flexed. The electrodes may be printed onto a single sheet, which is on the film.

As a third example, the transducer array 110 includes a flexible mat, a receiver layer of piezoelectric material on one side of the flexible mat, and a transmitter layer of piezoelectric material on an opposite side of the flexible mat. A plurality of electrodes are on the piezoelectric material of the receiver layer, and a plurality of electrodes are on the piezoelectric material of the transmitter layer. The electrodes on the receiver layer may be perpendicular or angled with respect to the electrodes on the transmitter layer. Each transducer element 120 is formed by an overlapping portion of an electrode in the transmitter layer with an electrode in the receiver layer.

The electrodes are not limited to any particular geometry. Width and thickness may be constant or varying. Geometry may even vary. For instance, an electrode may have rectangular portions and hexagonal or circular portions.

The flexible transducer array 110 may be mounted on a flexible circuit board. The circuit board may be a made of a dielectric such as Kapton® polyimide film.

As discussed below, the flexible ultrasonic transducer array 110 will be subjected to curing temperatures and pressures. Therefore, the piezoelectric material is selected to withstand such temperatures and pressures (the temperatures and pressures will, of course, depend upon the material being cured). Examples of piezoelectric materials that can withstand temperatures and pressures for curing fiber reinforced composites include, without limitation, calcium oxyborate, langanite, and bismuth titanate.

Figure 2:
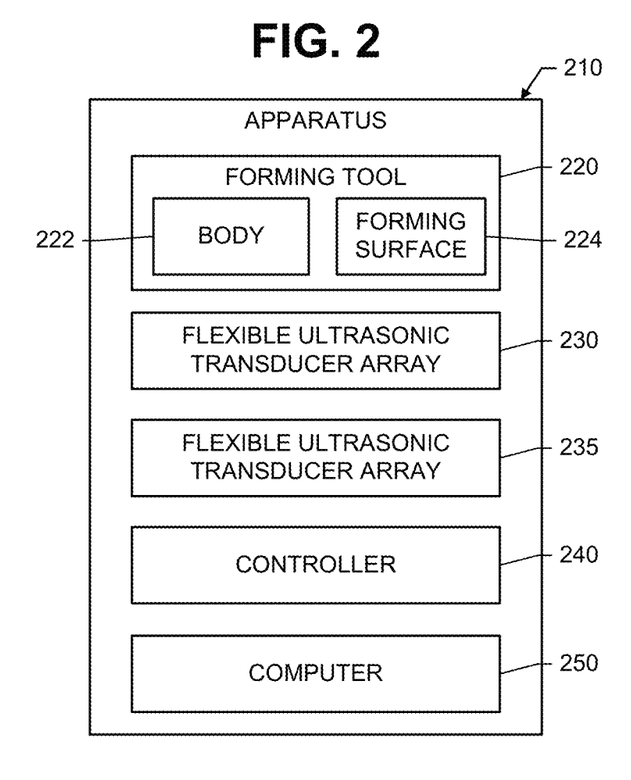
FIG. 2 is an illustration of an apparatus including a forming tool and a flexible ultrasonic transducer array.

Reference is made to FIG. 2, which illustrates an apparatus 210 including a tool 220 for forming a part. The tool 220 includes a body 222 having a forming surface 224. The forming surface 224 may have a non-planar shape. Examples of tools 220 include, but are not limited to, mandrels, injection molds, resin transfer molds, and press molds.

The apparatus 210 further includes a flexible ultrasonic transducer array 230 on the forming surface 224. The ultrasonic transducer array 230 may cover the entire forming surface 224 or it may partially cover the forming surface 224. For example, the transducer array 230 may only cover select areas of interest of the forming surface 224.

As used herein, the term "on the forming surface" may mean direct physical contact with the forming surface. The term "on the forming surface" may also mean spaced apart from the forming surface, for example, by a thin layer (e.g., a layer of adhesive) or spaced apart by the part being fabricated. When on the forming surface 224, the ultrasonic transducer array 230 conforms to the shape of the forming surface 224. The flexibility of the array 230 enables the array to conform to the shape of the forming surface 224.

The flexible transducer array 230 may be secured to the tool 220. For instance, the array 230 may be mechanically clamped to the tool 220, adhesively bonded to the tool 220, or vacuum bagged down against the tool 220. In some instances, the flexible transducer array 230 may not be secured and may instead sit on the tool 220.

The tool 220 may be used to fabricate a part made of a material such as fiber reinforced plastic ("FRP"). An FRP part may be fabricated by laying up a ply stack on the forming surface 224 of the forming tool 220. The ply stack may include one or more plies of fabric. For instance, the ply stack may include one or more plies of carbon fibers or some other type of reinforcing fiber. The ply stack may be pre-impregnated with resin before being deposited on the forming surface 224. In the alternative, a dry ply stack may be deposited on the forming surface 224 and thereafter infused with resin. The resin-impregnated ply stack is then cured under high temperature and pressure. Resulting is the FRP part.

The FRP part may have structural inconsistencies such as delaminations, and foreign object debris. The ultrasonic testing reveals these inconsistencies.

The apparatus 210 may further include an array controller 240 for operating the transducer array 230. If the transducer array 230 is operated in pulse echo (PE) ultrasonic mode, the controller 240 causes the transducer array 230 to generate a sound beam that enters a front surface of the FRP part, hits the back wall, and is reflected back towards the transducer array 230. The reflected signal returns to the origination transducer, which measures the reflected acoustic energy. If a structural inconsistency is in the path of the sound beam, the structural inconsistency will reflect the sound beam back to the transducer array 230. A sound beam reflected off a structural inconsistency will arrive at the transducer array 230 sooner than a sound beam reflected off the back wall.

The transducer array 230 may have multiple time gates. A time gate refers a window of analysis in time and amplitude. Gates are typically used to filter out data from wedges, front surfaces, etc. A time gate for pulse echo is usually set to find reflections within the part, after the front surface of the FRP part.

The apparatus 210 may further include a second transducer array 235 on an opposite side of the FRP part. The controller 240 may operate both transducer arrays 230 and 235 in through-testing ultrasonic (TTU) mode. The controller 240 causes one of the transducer arrays to generate sound pulses that are transmitted through a front surface of the FRP part, and continues to the other one of the transducer arrays. The controller 240 causes the other one of the transducer arrays to measure the transmitted acoustic energy transmitted through the back wall of the FRP part. For TTU, the time gate is set across the entire FRP part.

The apparatus 210 may further include equipment such as a computer 250 for processing the PE data and/or TTU data. For instance, the computer 250 may convert the PE data and/or TTU data into a data representation (e.g., a C-scan) that identifies any structural inconsistencies in the FRP part.

The apparatus 210 may be used in the aircraft industry to validate the health (e.g., integrity and fitness) of large aircraft parts. The apparatus 210 may perform ultrasonic inspection of a large FRP part without having to transfer the FRP part to a separate inspection station. Moreover, the apparatus 210 may perform the ultrasonic inspection without a robotic multi-axis scanning system scanning a transducer array over the FRP part. Ultrasonic testing with the apparatus 210 is less capital intensive, less labor expensive, and faster to perform.

The apparatus 210 also eliminates need to determine position of the transducer array 230 along the cured part. Consider conventional ultrasonic inspection that includes scanning a transducer array along an FRP part, and using an encoder to record position of the transducer array as it is being scanned. The apparatus 210 eliminates the need for the encoder, and it eliminates the need to correlate the PE data with the position, since the flexible ultrasonic transducer array 230 is fixed relative to the FRP part during inspection.

The following paragraphs will describe different configurations of the apparatus 210 and different methods of performing ultrasonic testing.

Figure 3:
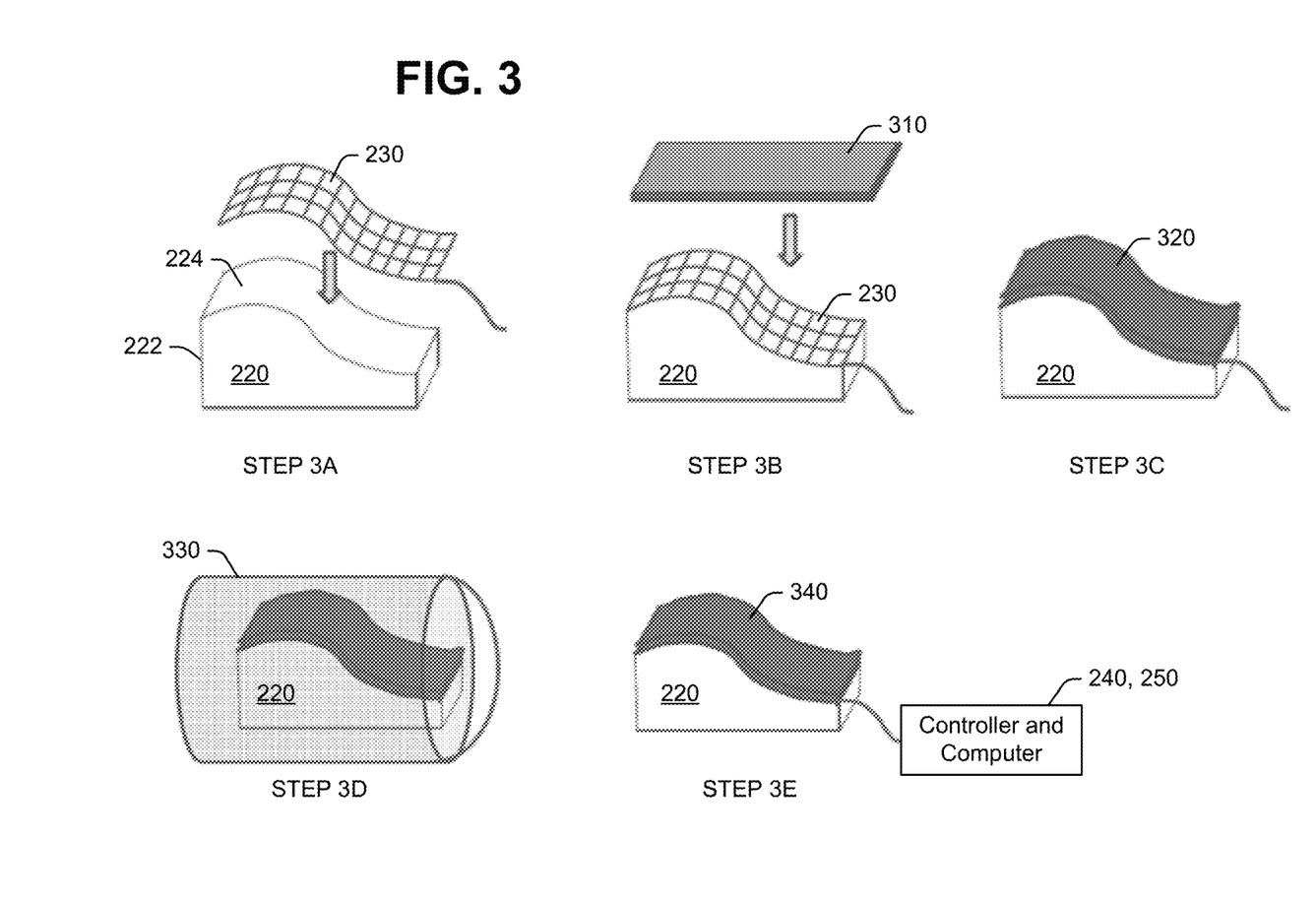
FIGS. 3, 4, 5 and 6 are illustrations of different methods of using a forming tool and a flexible ultrasonic transducer array to fabricate a fiber reinforced plastic part.

Reference is made to FIG. 3, which illustrates a first method of using a forming tool 220 and a flexible transducer array 230 to fabricate an FRP part. The forming tool 220 of FIG. 3 has a forming surface 224 with a compound curvature.

At steps 3A and 3B, the flexible transducer array 230 is placed on the forming surface 224 and secured to the forming surface 224. That is, the transducer array 230 is placed on the "tool side." The transducer array 230 conforms to the forming surface 224 and is in direct contact with the forming surface 224.

Also at step 3B, a ply stack 310 is placed on the transducer array 230, and conforms to the compound curvature of the forming surface 224. The ply stack 310 may be pre-impregnated with resin prior to being placed on the forming surface 224.

A parting layer (not shown) may be placed between the transducer array 230 and the ply stack 310. The parting layer will facilitate separating the transducer array 230 from a cured part.

If a smooth finish for the part is desired, a caul may be placed between the ply stack 310 and the transducer array 230. In the alternative, the transducer array 230 may be encapsulated in a material (e.g., rubber or silicone) that functions as a caul.

At step 3C, the ply stack 310 is bagged with a vacuum bag 320. The transducer array 230 is located underneath the vacuum bag 320.

At step 3D, the forming tool 220 is placed in an autoclave 330, wherein the ply stack 310 is exposed to curing temperature and pressure to produce an FRP part 340. Because the transducer array 230 is also underneath the vacuum bag 320 during curing, it too is exposed to the curing temperature and pressure.

At step 3E, the forming tool 220 is removed from the autoclave 330, and ultrasonic inspection of the FRP part 340 is performed. The transducer array 230 is already acoustically coupled to the FRP part 340. In some instances, the parting layer, caul, or encapsulation material may provide a coupling medium. In other instances, air coupling may be utilized. The air coupling may be utilized for lower resolution, lower frequency inspection. The transducer array 230 is connected to a controller 240, which operates the transducer array 230 in pulse echo mode to generate PE data. A computer 250 processes the PE data to determine structural health of the FRP part 340. The inspection may be performed before or after the vacuum bag 320 has been removed from the cured part 340. After the cured part 340 has been inspected, it is separated from the transducer array 230 and moved off the forming tool 220.

Certain operations may be performed on the FRP part 340 after it is removed from the autoclave 330, but prior to ultrasonic inspection. For example, the FRP part 340 may be machined prior to ultrasonic inspection.

Figure 4:
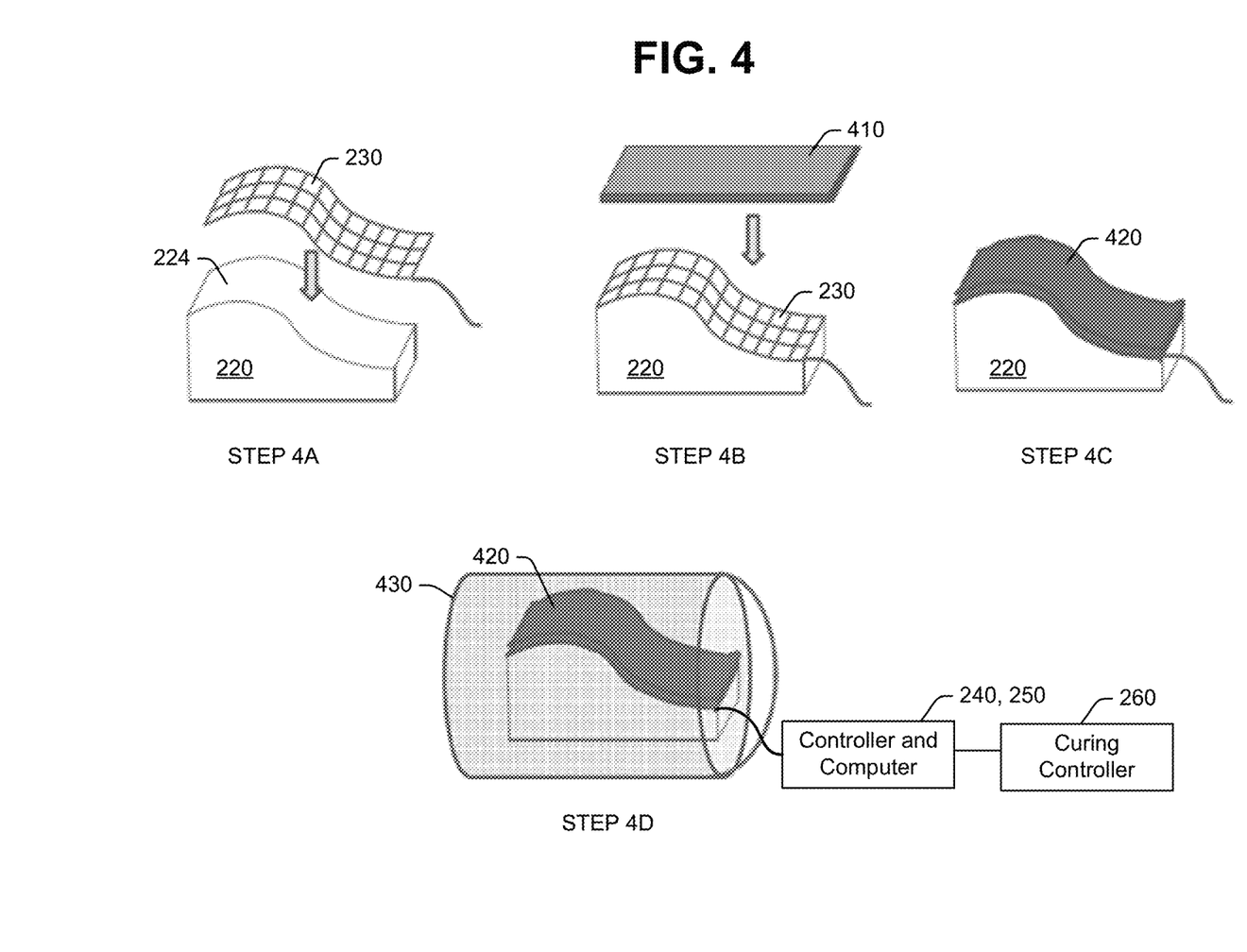

Reference is made to FIG. 4, which illustrates a second method of using a forming tool 220 and a flexible transducer array 230 to fabricate an FRP part. The second method is a variation of the first method in that inspection is performed during curing instead of after curing.

Steps 4A, 4B and 4C are performed in the same manner as steps 3A, 3B and 3C. That is, a transducer array 230 is placed on the forming surface 224 of a forming tool 220, a ply stack 410 is placed on the transducer array 230, and the ply stack 410 is bagged with a vacuum bag 420.

At step 4D, the forming tool 220 is placed in an autoclave 430, wherein the ply stack 410 is exposed to curing temperature and pressure. While the ply stack 410 is being cured, the controller 240 and computer 250 obtain and process pulse echo data from the transducer array 230.

The ply stack 410 may be cured according to a profile. Certain parameters of the profile may be changed in response to the PE data obtained during the curing. Parameters such as temperature and pressure may be adjusted according to thickness (time-of-flight) or signal attenuation information. These parameters may be adjusted on the fly, or they may be used to adjust the profile for curing future parts.

In addition, the PE data obtained during curing may be used to change tool and caul design. If the PE data identifies locations where porosity is forming, caul sheets may be adjusted to increase pressure locally.

The PE data may be used to terminate the curing prematurely. For instance, if the PE data reveals that foreign material is present early, the curing may be aborted. If the PE data reveals that the part will not pass inspection, the curing may be aborted.

The curing may be controlled by an independent curing controller 260. The computer 250 may analyze the pulse echo data and communicate the results to the curing controller 260, or the computer 250 may send the PE data to the curing controller 260, which then analyzes the PE data.

Figure 5:
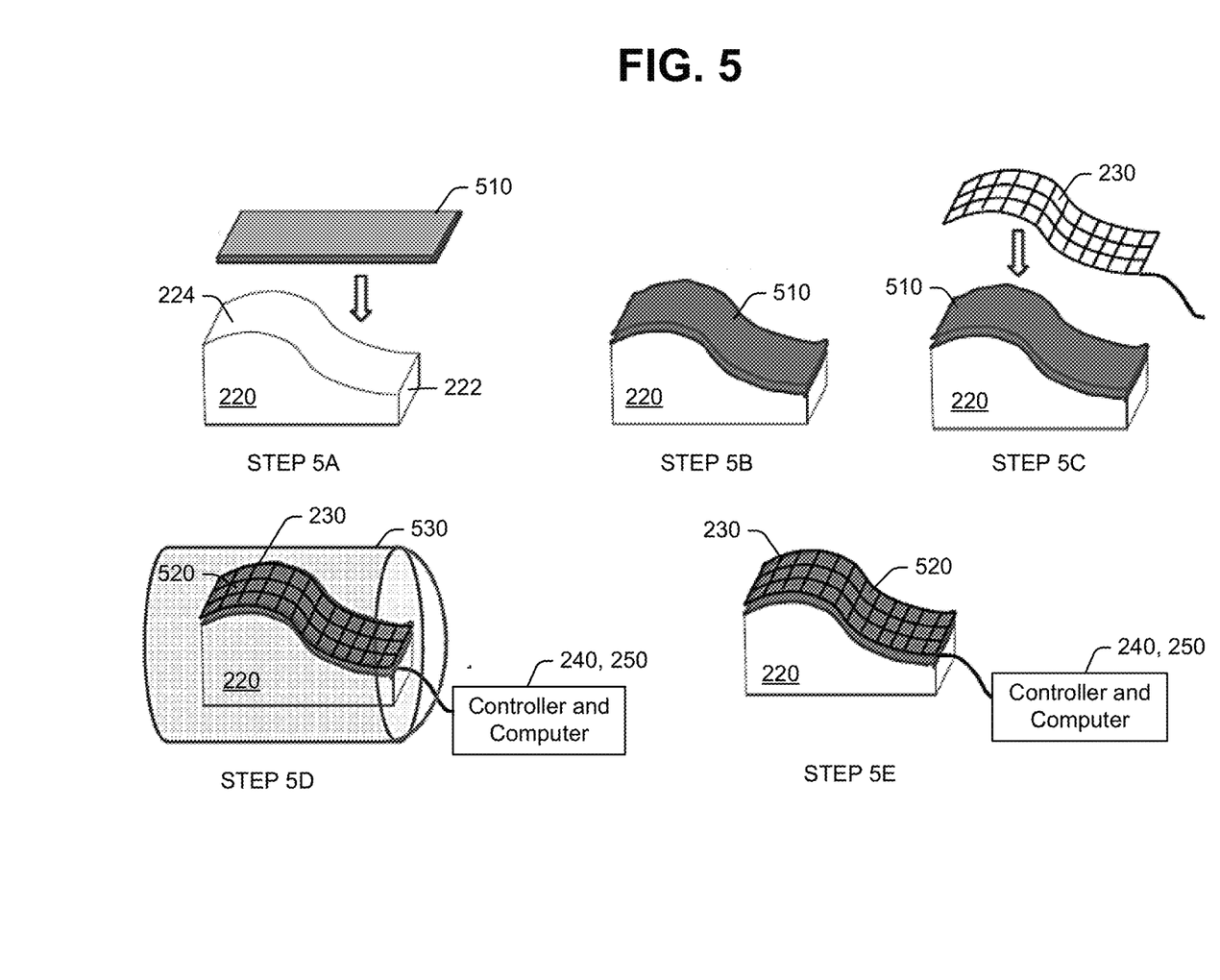

Reference is made to FIG. 5, which illustrates a third method of using a forming tool 220 and the flexible transducer array 230 to fabricate an FRP part. At steps 5A and 5B, a ply stack 510 is placed on a forming surface 224 of the forming tool 220. At step 5C, the transducer array 230 is placed on the ply stack 510. That is, the transducer array 230 is placed on the "bag side" of the ply stack 510.

At step 5D, the ply stack 510 is bagged with a vacuum bag 520, and the forming tool 220 is placed within an autoclave 530. While the ply stack 510 is being cured or after cool-down, the controller 240 and the computer 250 may obtain and process PE data from the transducer array 230. Step 5E may be performed in addition, or in the alternative, to step 5D. At step 5E, the PE data may be obtained and processed after the forming tool 220 has been removed from the autoclave 530.

Figure 6:
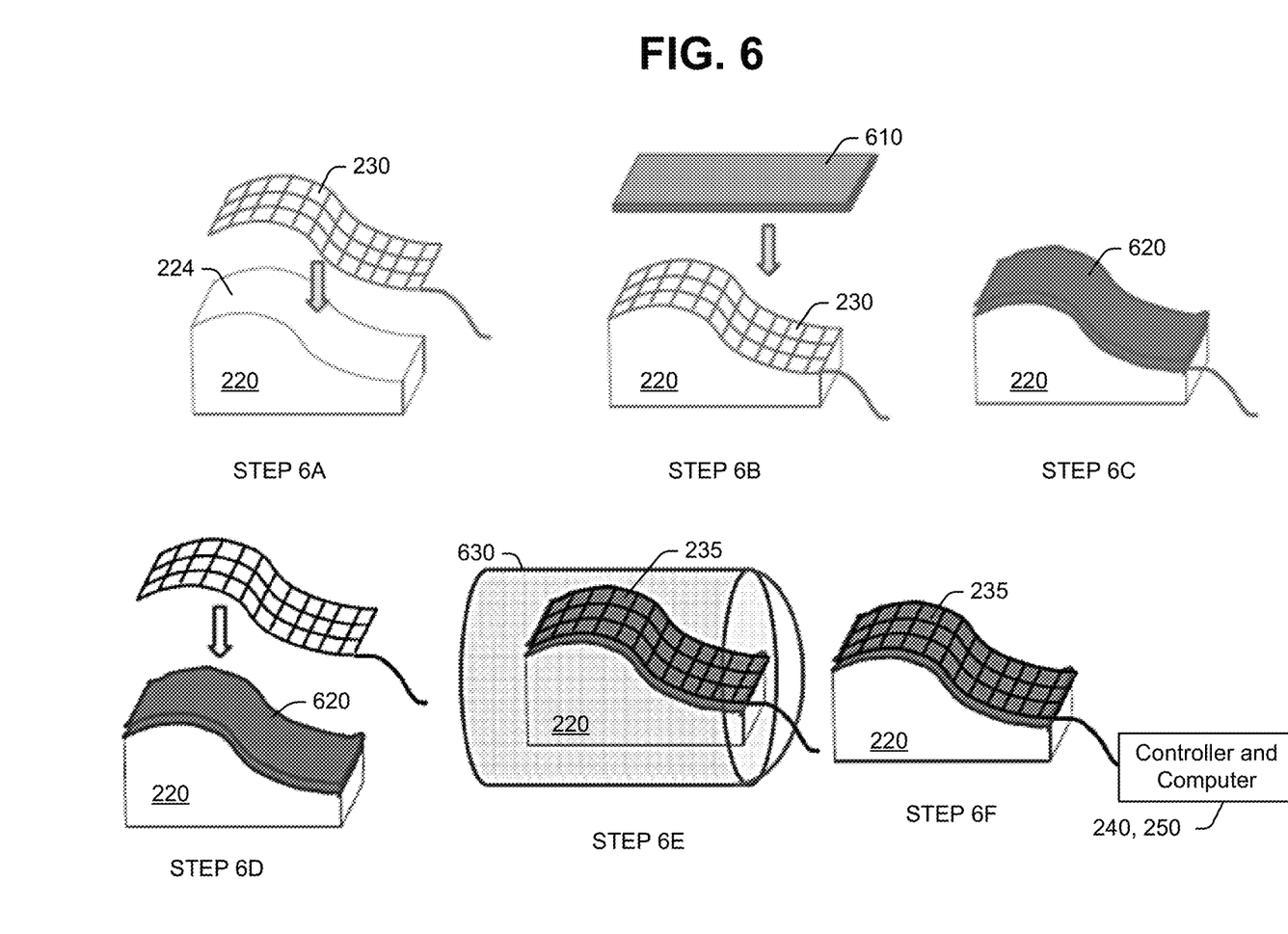

Reference is made to FIG. 6, which illustrates a fourth method of using a forming tool 220 and first and second flexible transducer arrays 230 and 235 to fabricate an FRP part. At step 6A, the first transducer array 230 is placed on the forming surface 224 of the forming tool 220. At step 6B, a ply stack 610 is placed on the first transducer array 230. At step 6C, the ply stack 610 is bagged with a vacuum bag 620.

At step 6D, the second transducer 235 is placed on the vacuum bag 620, over the ply stack 610. The vacuum bag 620 will provide acoustic coupling for the second transducer array 235.

At step 6E, the bagged ply stack 610 and the transducer arrays 230 and 235 are placed within an autoclave 630. While the ply stack 610 is being cured or after cool-down, the controller 240 and computer 250 obtain and process TTU data from the transducer arrays 230 and 235. At step 6F, In addition, or in the alternative, the TTU data may be obtained and processed after the forming tool 220 has been removed from the autoclave 630. In addition to obtaining through transmission data from both arrays 230 and 235, one of the arrays 230 or 235 may be used to obtain PE data.

Figure 7:
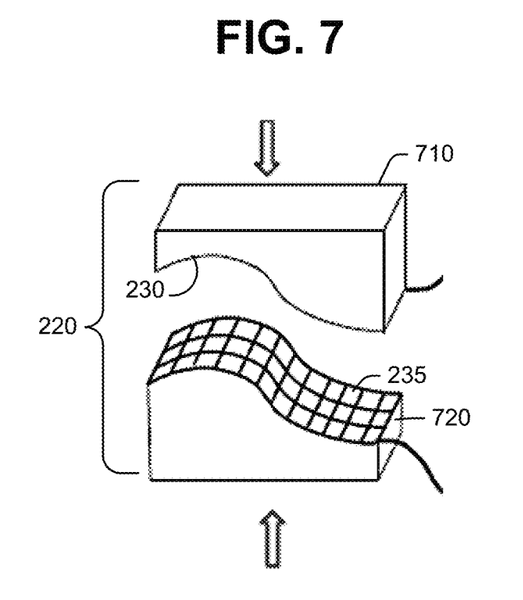
FIGS. 7 and 8 are illustration of molds and flexible ultrasonic transducer arrays for forming molded parts.

Reference is made to FIG. 7, which illustrates a mold 220 for forming a composite part. The part may be made formed from a material such as plastic, rubber, metal, fiber reinforced plastic, ceramic, or a combination thereof. Examples of the mold 220 include an injection mold, resin transfer mold, and a press mold.

The mold 220 may include first and second halves 710 and 720. First and second flexible ultrasonic transducer arrays 230 and 235 are located on forming surfaces of the first and second halves 710 and 720. PE data and/or TTU data may be collected while the part is still in the mold 220. PE data and/or TTU data may be obtained after initial shaping or injection/resin transfer, and during curing.

Figure 8:
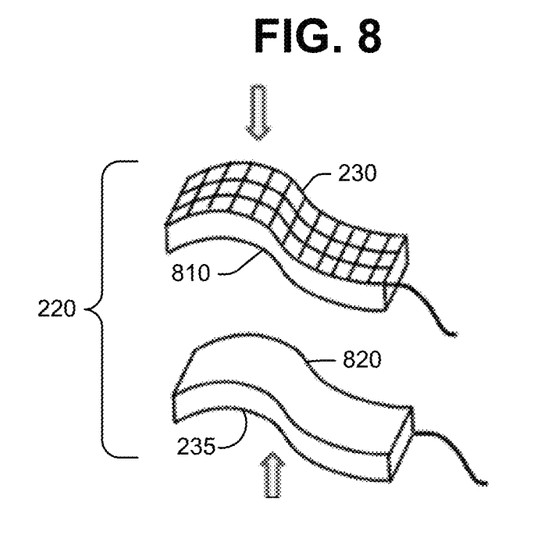

FIG. 8 also shows a mold 220 including first and second halves 810 and 820. Transducer arrays 230 and 235 are located on outer surfaces of the mold halves 810 and 820 instead of the forming surfaces. Part mark-off is avoided by placing the transducer arrays 230 and 235 on the outer surfaces of the mold halves 810 and 820.

If resin infusion or resin transfer molding is performed, the computer 250 (not shown in FIGS. 7 and 8) may use the TTU data to track a liquid resin front moving through the ply stack or mold. The resin flowing into the ply stack or mold creates a coupled path for the ultrasound (stress waves) to travel from the sending transducer array to the receiving transducer array. A negligible level of ultrasound travels across the dry material because the impedance mismatch between air and dry material, and the transducer array or mold material is very high. The resin provides a good ultrasound path, which results in a higher signal at the receiving transducer array. By tracking the liquid resin front, complete wetting may be ensured, and void movement may be tracked and voids eliminated.

The methods described above use a forming tool for fabricating a new part. However, a method herein is not so limited. For example, the forming tool may be used to apply a repair patch to a damaged part.

Figure 9:
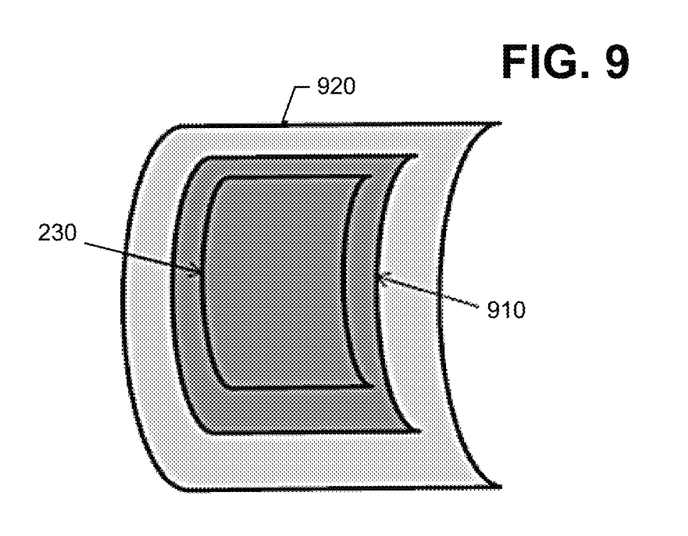
FIG. 9 is an illustration of an apparatus including a heat blanket and a flexible ultrasonic transducer array.

Reference is made to FIG. 9, which illustrates a forming tool including a heat blanket 910. The heat blanket 910 may include a set of insulated wires sandwiched inside a medium that distributes heat and that is surrounded by rubber. The wires heat up when subjected to an electric current, and the medium generates an area of (mostly) uniform heating.

A flexible ultrasonic transducer array 230 is secured to a surface of the heat blanket 910, or it is embedded with the heat blanket 910.

To repair a damaged area of a composite structure 920, the damaged area is removed, and a patch (not shown) of resin-impregnated composite is placed within the removed area. The blanket 910 is placed over the patch. The blanket 910 is heated to cure the patch. During curing and/or after curing, PE data is collected from the transducer array 230. The PE data is processed to identify any structural inconsistencies in the patch during and/or after curing.

In the methods described above, the cured or molded part may be separated from the forming tool or mold. However, a method herein is not so limited. For instance, the transducer array 230 may be co-cured or co-bonded with a composite part during curing. After curing, the transducer array 230 is separated from the forming tool 220. The transducer array 230 is embedded in the part.

Figure 10:
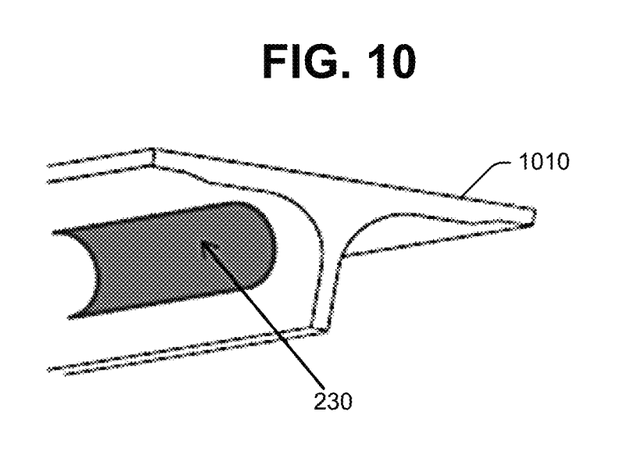
FIG. 10 is an illustration of a composite part with an embedded flexible ultrasonic transducer array.

Reference is made to FIG. 10, which illustrates a composite part 1010 with an embedded flexible transducer array 230. An advantage of embedding the transducer array 230 in the part 1010 is that it allows in-situ inspection of the part 1010. As some examples, in-situ inspection may be used to monitor damage growth in mechanical testing or to provide structural health monitoring (SHM) in "hot spots" or limited access areas. The embedded array 230 may replace individual transducers typically used for in-situ NDI, thereby significantly increasing sensitivity to damage and improving the tracking of growth of structural inconsistencies. Individual transducers inspect locally for growth. They are typically spaced apart, so growth in between the individual transducers may be missed. A flexible transducer array having crossing electrodes may be designed to essentially track growth at any point on the part 1010.

Although not so limited, the part 1010 is shown with a rounded 3-D corner. Sharp corner radii are sometimes more difficult to inspect. The flexible ultrasonic transducer array simplifies the inspection of sharp corner radii.

The apparatus and methods described above utilize an ultrasonic transducer array that is flexible. In some instances, however, a rigid ultrasonic transducer array may be used. As a first example, a rigid array may be pre-molded to fit on the forming surface of a forming tool. As a second example, the forming surface and the transducer array may be planar.

The invention claimed is:

1. Apparatus for fabricating an aircraft part from an uncured, fiber reinforced plastic ply stack, the apparatus comprising:
    an aircraft part forming tool having a forming surface;
    a heater configured to selectively heat the forming surface of the forming tool to a curing temperature sufficient to cure the fiber reinforced plastic ply stack;
    a first ultrasonic transducer array on the forming surface and having an array surface configured to receive the uncured fiber reinforced plastic ply stack; and
    a controller and computer operatively coupled to the heater and the first ultrasonic transducer array, the controller and computer configured to:
        operate the heater to heat the forming surface of the forming tool to the curing temperature, with the first ultrasonic transducer array on the forming surface of the part forming tool and the fiber reinforced plastic ply stack on the first ultrasonic transducer array; and
        with the fiber reinforced plastic ply stack still on the first ultrasonic transducer array, obtain and process ultrasonic data from the first ultrasonic transducer array, during or after operation of the heater.

2. The apparatus of claim 1, wherein the first ultrasonic transducer array includes a plurality of transducer elements arranged in a pattern.

3. The apparatus of claim 1, wherein the forming surface is curved, and wherein the first ultrasonic transducer array is a first flexible ultrasonic transducer array that conforms to the curved forming surface.

4. The apparatus of claim 1, wherein the first ultrasonic transducer array is in direct contact with the forming surface and conforms to the forming surface.

5. The apparatus of claim 1, wherein the first ultrasonic transducer array is in contact with the forming surface and conforms to the forming surface with the ply stack on the first array; and the apparatus further comprises a second flexible ultrasonic transducer array on the ply stack.

6. The apparatus of claim 1, wherein the controller and computer are configured for obtaining and processing through transmission ultrasonic data from the first ultrasonic transducer array.

7. The apparatus of claim 6, wherein the computer uses the through transmission ultrasonic data to track a liquid resin front.

8. The apparatus of claim 1, wherein the controller and computer are configured for obtaining and processing pulse echo data from the first ultrasonic transducer array.

9. The apparatus of claim 8, wherein the controller and computer are configured to collect and process the pulse echo data during heating of the ply stack to the curing temperature.

10. The apparatus of claim 9, wherein the controller is configured for controlling the curing temperature according to a profile; and wherein certain parameters of the profile are changed in response to the pulse echo data obtained during the curing.

11. The apparatus of claim 1, further comprising a vacuum bag over the aircraft part forming tool, wherein the first ultrasonic transducer array is underneath the bag.

12. The apparatus of claim 1, wherein the forming tool is a first forming tool of a mold; and wherein the apparatus further comprises a second forming tool of the mold, the first and second tools configured to form an aircraft part.

13. The apparatus of claim 1, wherein the tool includes a heat blanket; and wherein the first ultrasonic transducer array is on a surface of the heat blanket.

* * * * *